United States Patent
Lion

(10) Patent No.: US 7,423,104 B2
(45) Date of Patent: Sep. 9, 2008

(54) HYPERBRANCHED COPOLYMER COMPRISING MONOMERS OF CHOICE, A COMPOSITION, AND A COSMETIC METHOD

(75) Inventor: Bertrand Lion, Paris (FR)

(73) Assignee: L'Oreal, S.A., Paris (FR)

( * ) Notice: Subject to any disclaimer, the term of this patent is extended or adjusted under 35 U.S.C. 154(b) by 98 days.

(21) Appl. No.: 11/192,062

(22) Filed: Jul. 29, 2005

(65) Prior Publication Data

US 2006/0030686 A1 Feb. 9, 2006

Related U.S. Application Data

(60) Provisional application No. 60/613,507, filed on Sep. 28, 2004.

(30) Foreign Application Priority Data

Jul. 29, 2004 (FR) .................................. 04 08373

(51) Int. Cl.
*C08F 220/68* (2006.01)
(52) U.S. Cl. ................. 526/317.1; 526/318; 526/318.4; 526/319; 526/324; 526/325; 526/328.5
(58) Field of Classification Search .............. 526/317.1, 526/318, 318.4, 319, 324, 325, 328.5
See application file for complete search history.

(56) References Cited

U.S. PATENT DOCUMENTS

| 4,542,171 A | 9/1985 | Elser et al. |
| 5,625,005 A | 4/1997 | Mallya et al. |
| 6,552,146 B1 * | 4/2003 | Mougin ...................... 526/319 |

FOREIGN PATENT DOCUMENTS

| EP | 0 096 459 | 12/1983 |
| EP | 0 815 848 | 1/1988 |
| EP | 0 348 565 A1 | 1/1990 |
| EP | 0 895 467 | 2/1999 |
| WO | WO 97/18247 | 5/1997 |
| WO | WO 97/35541 | 10/1997 |
| WO | WO 99/03894 | 1/1999 |
| WO | WO 01/96429 A1 | 12/2001 |
| WO | WO 03/072621 A1 | 9/2003 |
| WO | WO 2004/078809 A1 | 9/2004 |

OTHER PUBLICATIONS

Hugenberg et al., "Synthesis and large scale fractionation of non-linear polymers: brushes and hyperbranched polymers," Journal of Non-Crystalline Solids, 307-310 (2002), pp. 765-771.

Yoo et al., "Synthesis of Hyperbranched Polyacrylates in Emulsion by Atom Transfer Radical Polymerization," Macromolecules 2002, 35(4), pp. 1146-1148.
Gaynor et al., "Branched and Hyperbranched Macromolecules by Atom Transfer Radical Polymerization," (1996), vol. 37(2), pp. 413-414.
Coessens et al., "Functional polymers by atom transfer radical polymerization," Prog. Polym. Sci. 26 (2001) pp. 337-377.
Simon, "Synthesis of Hyperbranched and Highly Branched Methacrylates by Self-Condensing Group Transfer Copolymerization," Macromolecules (2001), 34(18), pp. 6206.6213.
Matyjasezwski et al., "Controlled/"Living" Radical Polymerization. Atom Transfer Radical Polymerization in the Presence of Transition-Metal Complexes," J. Am. Chem. Soc. (1995), 117, pp. 5614-5615.
Kobatake et al., "Synthesis of Nitroxy-Functionalized Polybutadiene by Anionic Polymerization Using a Nitroxy-Functionalized Terminator," Macromolecules, (1997), 30(14), pp. 4238-4242.
Malmström, "Macromolecular engineering via 'living' free radical polymerizations," Macromol. Chem. Phys. (1998), 199(6), pp. 923-935.
Charleux et al., "Synthesis of Branched Polymers by Cationic Polymerization," Advances in Polymer Science, (1999), 142, pp. 1-69.
Grulke, "Solubility Parameter Values," Polymer Handbook (3d ed.), Chapter VII, pp. 519-559.
Hansen, "The Three Dimensional Solubility Parameter—Key to Paint Component Affinities: I. Solvents, Plasticizers, Polymers, and Resins," J. Paint Technol., (1967), 39(505), pp. 105-117.
French Search Report for French Priority Application No. 04/08373, dated Feb. 11, 2005.
English language esp@cenet abstract for EP 0 815 848.
English language Derwent abstract of EP 0 895 467.

* cited by examiner

*Primary Examiner*—Robert D. Harlan
(74) *Attorney, Agent, or Firm*—Finnegan, Henderson, Farabow, Garrett & Dunner, L.L.P.

(57) ABSTRACT

Disclosed is a hyperbranched copolymer comprising at least two polymeric branches, which may be identical or different, each comprising at least one at least trifunctional branch point, wherein a first polymeric branch comprises at least one first monomer chosen from isobornyl acrylate, isobornyl methacrylate, isobutyl acrylate, isobutyl methacrylate and 2-ethylhexyl acrylate, a second polymeric branch comprises at least one second monomer chose from isobornyl acrylate, isobornyl methacrylate, isobutyl acrylate, isobutyl methacrylate and 2-ethylhexyl acrylate.

Also disclosed is a cosmetic or pharmaceutical composition, for example, a dermatological composition, comprising said hyperbranched copolymer. Further disclosed is a cosmetic method of making up or caring for keratin materials, comprising applying to said materials a cosmetic composition comprising said hyperbranched copolymer.

47 Claims, No Drawings

HYPERBRANCHED COPOLYMER COMPRISING MONOMERS OF CHOICE, A COMPOSITION, AND A COSMETIC METHOD

This application claims benefit of U.S. Provisional Application No. 60/613,507, filed Sep. 28, 2004, the contents of which are incorporated herein by reference.

This application also claims benefit of priority under 35 U.S.C. § 119 to French Patent Application No. 04 08373, filed Jul. 29, 2004, the contents of which are also incorporated by reference.

The present disclosure pertains to new hyperbranched copolymers and also to compositions, for example, cosmetic or pharmaceutical compositions, and further, for example, topical dermatological compositions, comprising said copolymers; it also relates to the use of these copolymers, for example, in the field of making up and/or caring for keratin materials, for example, the skin of the body or of the face, and the lips.

Within the field of cosmetology a frequent aim is to have compositions available that allow a deposit, for example, an adhesive or film-forming deposit, to be obtained on the keratin materials in question, such as the skin, lips, hair, eyelashes or nails.

For example, these compositions are able to provide color (makeup or hair coloring compositions), gloss or mattness (skin makeup or care compositions), physical properties such as shaping, (hair compositions, for example, styling compositions), and properties of care or protection (care compositions, for example moisturizing or UV-protection compositions).

The aim is generally that the cosmetic deposit should have good persistence and staying power over time and also good adhesion to the substrate. For example, it is desirable for this deposit to be able to withstand mechanical attacks such as rubbing and transfer by contact with another object, and also to withstand water, perspiration, tears, rain, sebum, and oils. This is particularly true in the makeup field, for example, in the sector of lipsticks, where there is a desire for prolonged colorfastness and gloss staying power, and for transfer resistance of the color; within the sector of foundations, eyeshadows and powders, where there is a desire for the color provided to be fast, with the mattness of the initial makeup being maintained for as long as possible despite the secretion of sebum and perspiration, and also for transfer resistance. Moreover, makeup compositions must be comfortable to wear and must not have too sticky a texture.

In order to reconcile the entirety of these properties, which are often mutually contradictory, within a single composition, it is possible to employ a blend of two or more polymers, very different in chemical nature, each polymer providing one of the desired characteristics. Nevertheless, the use of a blend of polymers having different chemical natures, not necessarily compatible with one another, may give rise to problems of separation within the composition.

The use of random polymers, for example of conventional acrylic polymers obtained by conventional free-radical polymerization by statistical mixing of monomers, does not allow these problems to be solved satisfactorily. The reason for this is that the random polymers known previously exhibit a dispersity in terms of composition of the polymeric chains, which also leads to separation of the polymers within the formula.

Also known are hyperbranched polymers, which have been proposed for use in hair cosmetology, in PCT Application No. WO 01/96429; these hyperbranched polymers are prepared from a first type of acrylic monomers and from branching monomers possessing two polymerizable functions with different reactivities, to give polymers comprising pendant allylic units, which can be polymerized subsequently in the presence of a second type of acrylic monomers.

However, the polymers described in PCT Application No. WO 01/96429 are soluble in aqueous media and are difficult to formulate in the lipophilic media that are generally employed in cosmetology, such as oily media or solvents. Certain cosmetic makeup compositions, though, such as lipsticks and foundations, very generally comprise a fatty phase.

The aim of at least one embodiment of the present disclosure is to overcome at least one drawback discussed above by providing new, specific hyperbranched copolymers which in at least one embodiment evades the problems of separation within the formula while at the same time allowing the desired cosmetic properties to be provided. In at least one embodiment, these polymers are easy to formulate in the lipophilic media of cosmetic compositions.

An embodiment of the present invention is a hyperbranched copolymer comprising at least two, for example, three, polymeric branches, which may be identical or different, each comprising at least one at least trifunctional branch point, wherein a first polymeric branch comprises at least one first monomer chosen from isobornyl acrylate, isobornyl methacrylate, isobutyl acrylate, isobutyl methacrylate and 2-ethylhexyl acrylate, a second polymeric branch comprises at least one second monomer chose from isobornyl acrylate, isobornyl methacrylate, isobutyl acrylate, isobutyl methacrylate and 2-ethylhexyl acrylate. Another embodiment is a cosmetic or pharmaceutical composition, for example, a dermatological composition, comprising said copolymer.

In an embodiment, the polymers according to the invention may have the advantage of allowing a film to be obtained which may be flexible and not at all sticky.

As used herein, "Hyperbranched polymers" means polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain.

The branches may be, for example, connected to one another by a polyfunctional compound, for example, a compound as defined later or in the description, which, for example, has different reactivities.

As used herein, "trifunctional branch point" means the junction point between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points between at least three polymeric branches, for example n polymeric branches, of which n−1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

As used herein, "hyperbranched polymer" does not encompass, for example:

branched or graft polymers, i.e. polymers composed of a main chain having multiple trifunctional branch points from each of which a linear side-chain emanates, wherein the side-chains may be composed of at least one block, these side-chains being identical or different in nature to or from the main chain, such as, for example, those described in document European Patent No. EP815848, relating to copolymers having a carbon/fluorine skeleton with a Tg ranging from 0 and 30° C. and to rigid grafts having a Tg of more than 25° C., or in PCT Application No. WO 97/35541, relating to copolymers having a rigid, hydrophilic vinyl/acrylic skeleton and flexible, hydrophobic grafts;

comb polymers (specific case of graft polymers), i.e. polymers composed of a main chain having multiple trifunctional branch points from each of which a linear side-chain emanates (Glossary of basic terms in polymer science/IUPAC/1996), the branch points being situated at regular intervals;

star polymers, i.e. those polymers all of whose branch points are located at a single point.

In one embodiment, the at least one hyperbranched polymers comprise at least two polymeric branches, forming either the main branch or a secondary branch, and each comprising at least one trifunctional branch point, different from and independent of one another, which may form at least two trifunctional branch points, different from and independent of one another, each branch point being arranged, for example, in the interior of at least one chain.

As a non-limiting example, the copolymers according to the invention may be considered as capable of illustration by the following scheme:

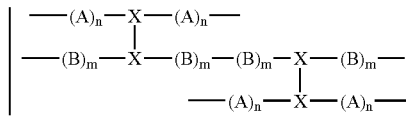

wherein A and B are chosen from the monomers of choice and/or additional monomers, as defined below, m and n being their degree of polymerization, and X is chosen from the trifunctional branching point which is present on each of the branches and may originate from a polyfunctional compound as defined below.

In an embodiment, the copolymers according to the invention may have the advantage of being easy to employ in organic cosmetic media, for example, media comprising lipophilic solvents and/or cosmetic oils, while retaining advantageous rheological properties.

For example, the copolymers according to the invention may exhibit good solubility in solvents, for example, lipophilic solvents, and/or in cosmetic oils.

As used herein, when a polymer is "soluble" in a medium means a polymer which does not form a precipitate but may, for example, form a clear solution in said medium at 25° C.

For example, the copolymer according to the disclosure is soluble at a concentration of at least 3% by weight in isododecane at 25° C. and 1 atm, for example, in a concentration of at least 5% by weight, further, for example, at least 10% by weight.

The copolymers according to the invention are therefore hyperbranched copolymers, i.e. copolymers comprising at least two, for example, at least three, polymeric branches, which can form either the main branch or a secondary branch, and each comprising at least one at least trifunctional branch point different from and independent of one another, for example, so as to form at least two at least trifunctional branch points, different from and independent of one another.

For example, the hyperbranched copolymers according to the disclosure contain units derived from at least one ethylenic monomer capable, for example, of undergoing free-radical polymerization, to form branches of said polymer, wherein each branch is in the form of a polymeric sequence of homopolymer kind or of random, alternating, block or gradient copolymer kind; for example, each branch is in the form of a homopolymer or of a linear random copolymer.

The copolymers according to the disclosure contain at least one first branch or polymeric sequence comprising at least one first monomer of choice, and at least one second sequence (or second branch) comprising at least one second monomer of choice, which may be identical to or different from said first monomer of choice.

As used herein, "monomer of choice" means monomers selected from the following list: isobornyl acrylate, isobornyl methacrylate, isobutyl acrylate, isobutyl methacrylate and 2-ethylhexyl acrylate.

Each branch or sequence may of course comprise a mixture of monomers of choice, it being possible for each branch to have a different chemical composition and/or structure.

In one embodiment are copolymers wherein the main branch is in the form of a homopolymer or random copolymer comprising 80% to 100% by weight, for example, 100% by weight, relative to the weight of the branch, of monomer(s) of choice.

In another embodiment are copolymers wherein the secondary branch or branches are in the form of a homopolymer or a random copolymer-comprising 80%-100% by weight, for example, 100% by weight, relative to the weight of the branch, of at least one monomer of choice.

The copolymer according to the disclosure may therefore comprise a first branch which will comprise a first monomer of choice, or else a mixture of at least two monomers of choice, for example, three monomers of choice, or else a mixture of one or two monomers of choice with at least one additional monomers as defined below.

The copolymer according to the disclosure may also comprise at least one second branch which may comprise a monomer of choice which is different from said first monomer of choice or identical to said first monomer of choice, which may also be alone or in a mixture with at least one other monomers of choice, and/or with at least one additional monomers as defined below.

For example, the total amount of monomers selected from the monomers of choice in the final copolymer ranges from, for example, 50% to 100% by weight, for example, from 60% to 98% by weight, further, for example, from 70% to 97% by weight, even further, for example, from 80% to 96% by weight, and even further, for example, from 90% to 95% by weight, of monomers of choice relative to the total weight of monomers present in the final copolymer.

The copolymer according to the disclosure may comprise, for example, 25% to 75% by weight, for example 30% to 70% by weight, of a first monomer of choice, which is present in a first branch, and 25% to 75% by weight, for example, 30% to 70% by weight, of a second monomer of choice, which may be present in the same branch or in another branch, the percentages being given relative to the total weight of monomers present in the final copolymer.

It may further comprise, optionally, from 1% to 40% by weight, for example, from 5% to 30% by weight, further, for example, 10% to 25% by weight, relative to the weight of the final copolymer, of at least one third monomer selected from the monomers of choice, the percentages being given relative to the total weight of monomers present in the final copolymer.

For example, copolymers may be chosen from—irrespective of whether in the same branch or in different branches—the following monomer combinations:
isobornyl acrylate and isobornyl methacrylate;
isobornyl acrylate and isobutyl acrylate;
isobornyl acrylate and isobutyl methacrylate;
isobornyl acrylate and 2-ethylhexyl acrylate;
isobornyl methacrylate and isobutyl acrylate;
isobornyl methacrylate and isobutyl methacrylate;
isobornyl methacrylate and 2-ethylhexyl acrylate;
isobornyl acrylate, isobornyl methacrylate and 2-ethylhexyl acrylate;
isobornyl acrylate, isobornyl methacrylate and isobutyl acrylate;
isobornyl acrylate, isobutyl methacrylate and 2-ethylhexyl acrylate;
isobornyl acrylate, isobutyl methacrylate and isobutyl acrylate; and
isobornyl methacrylate, isobutyl methacrylate and isobutyl acrylate.

For example, the copolymers may comprise:
isobornyl acrylate in the main branches and isobutyl acrylate in the secondary branches;
isobornyl acrylate in the main branches and 2-ethylhexyl acrylate in the secondary branches;
isobornyl methacrylate in the main branches and isobutyl acrylate in the secondary branches;
isobornyl methacrylate in the main branches and 2-ethylhexyl acrylate in the secondary branches;
isobornyl acrylate and isobornyl methacrylate in the main branches and isobutyl acrylate in the secondary branches;
isobornyl acrylate and isobornyl methacrylate in the main branches and 2-ethylhexyl acrylate in the secondary branches;
isobornyl acrylate and isobutyl methacrylate in the main branches and isobutyl acrylate in the secondary branches;
isobornyl acrylate and isobutyl methacrylate in the main branches and 2-ethylhexyl acrylate in the secondary branches;
isobornyl methacrylate and isobutyl methacrylate in the main branches and isobutyl acrylate in the secondary branches; or
isobornyl methacrylate and isobutyl methacrylate in the main branches and 2-ethylhexyl acrylate in the secondary branches.

The copolymer according to the disclosure may further comprise at least one additional monomer other than those selected from the monomers of choice.

This at least one additional monomer, or mixture of additional monomers, may be present in an amount ranging from 0 to 50% by weight, for example, from 2% to 40% by weight, further, for example, from 3% to 30% by weight, even further, for example, from 4% to 20% by weight, and even further, for example, from 5% to 10% by weight, relative to the total weight of monomers present in the final copolymer.

This at least one additional monomer may be selected, alone or in a mixture, from the following monomers, and also their salts, with the exception, of course, of the abovementioned monomers of choice:
(i) (meth)acrylates of formula $CH_2=CHCOOR$ or $CH_2=C(CH_3)COOR$ wherein R is chosen from:
   a linear or branched alkyl group comprising 1 to 30 carbon atoms, wherein said alkyl is optionally intercalated with at least one heteroatom selected from O, N, S and P, and/or wherein said alkyl group is optionally substituted by at least one substituent selected from —OH, halogen atoms (Cl, Br, I and F), —NR4R5, where R4 and R5, which may be identical or different, are chosen from hydrogen or a $C_1$ to $C_6$ linear or branched alkyl groups and phenyl groups; and polyoxyalkylene groups, for example, polyoxyethylene and/or polyoxypropylene, consisting of the repetition of 5 to 30 oxyalkylene units;
   a $C_3$ to $C_{12}$ cycloalkyl group, said cycloalkyl group being able to contain, in its chain, at least one heteroatom selected from O, N, S and/or P, and/or to be optionally substituted by at least one substituent selected from —OH and halogen atoms (Cl, Br, I and F);
   a $C_4$ to $C_{20}$ aryl or $C_5$ to $C_{30}$ aralkyl group (with a $C_1$ to $C_8$ alkyl group);

for example, R may be a methyl, ethyl, propyl, isopropyl, n-butyl, isobutyl, tert-butyl, hexyl, ethylhexyl, octyl, lauryl, isooctyl, isodecyl, dodecyl, cyclohexyl, t-butylcyclohexyl, stearyl, 2-ethylperfluorohexyl, 2-hydroxyethyl, 2-hydroxybutyl, 2-hydroxypropyl, methoxyethyl, ethoxyethyl, methoxypropyl, isobornyl, phenyl, 2-phenylethyl, t-butylbenzyl, benzyl, furfurylmethyl or tetrahydrofurfurylmethyl group, a methoxy-polyoxyethylene (or POE-methyl) group; a POE-behenyl or trifluoroethyl group; or a dimethylaminoethyl, diethylaminoethyl or dimethylaminopropyl group;
(ii) (meth)acrylamides of formula $CH_2=CHCONR4R5$ or $CH_2=C(CH_3)CONR4R5$ wherein R4 and R5, which may be identical or different, are chosen from
a) a hydrogen atom;
b) a linear or branched alkyl group comprising 1 to 18 carbon atoms, wherein said alkyl is optionally intercalated with at least one heteroatom selected from O, N, S and P; wherein said alkyl group may be optionally substituted by at least one substituent selected from hydroxyl groups, halogen atoms (Cl, Br, I and F) and Si(R4R5), wherein R4 and R5, which may be identical or different, are chosen from a $C_1$ to $C_6$ alkyl groups and phenyl groups; for example, a methyl, ethyl, propyl, isopropyl, n-butyl, isobutyl, tert-butyl, hexyl, isohexyl, cyclohexyl, ethylhexyl, octyl, isooctyl, decyl, isodecyl, cyclodecyl, dodecyl, cyclododecyl, isononyl, lauryl, t-butylcyclohexyl or stearyl group; a 2-ethylperfluorohexyl group; or a $C_{1-4}$ hydroxyalkyl group such as 2-hydroxyethyl, 2-hydroxybutyl and 2-hydroxypropyl; or a $C_{1-4}$ alkoxy-C1-4 alkyl group such as methoxyethyl, ethoxyethyl and methoxypropyl,
c) a $C_3$ to $C_{12}$ cycloalkyl group, such as the isobornyl group, or a heterocycloalkyl group (with alkyl of 1 to 4 carbon atoms), such as furfurylmethyl or tetrahydrofurfurylmethyl,
d) a $C_4$ to $C_{20}$ aryl group such as a phenyl group, and
e) a $C_5$ to $C_{30}$ aralkyl group (with a $C_1$ to $C_8$ alkyl group) such as 2-phenylethyl, t-butylbenzyl or benzyl;
(iii) ethylenically unsaturated monomers comprising at least one carboxylic, phosphoric or sulphonic acid or anhydride function, such as, for example, acrylic acid, methacrylic acid, crotonic acid, maleic anhydride, itaconic acid, fumaric acid, maleic acid, styrenesulphonic acid, vinylbenzoic acid, vinylphosphoric acid or acrylamidopropanesulphonic acid; and the salts thereof;

(iv) vinyl ethers of formula R6O—CH=CH$_2$ or vinyl esters of formula R6-COO—CH=CH$_2$ wherein R6 is chosen from a linear or branched alkyl groups comprising from 1 to 22 carbon atoms or a cyclic alkyl group comprising from 3 to 6 carbon atoms and/or an aromatic group, for example, benzene, anthracene or naphthalene;

(v) vinyl compounds chosen from CH$_2$=CH—R9, CH$_2$=CH—CH$_2$—R9 or CH$_2$=C(CH$_3$)=CH$_2$—R9 wherein R9 is a hydroxyl, halogen (Cl or F) or NH$_2$ group or a group OR10 wherein R10 is chosen from phenyl groups; C$_1$ to C$_{12}$ alkyl groups (the monomer is a vinyl or allyl ether); acetamide groups (NHCOCH$_3$); OCOR11 wherein R11 is chosen from an alkyl group of 2 to 12 carbons which is linear or branched (the monomer is a vinyl or allyl ester); or a group selected from:

linear or branched alkyl groups of 1 to 18 carbon atoms, wherein said alkyl is intercalated with at least one heteroatom selected from O, N, S and P, wherein alkyl group is optionally substituted by at least one substituent selected from hydroxyl groups, halogen atoms (Cl, Br, I and F) and groups Si(R4R5), wherein R4 and R5, which may be identical or different, are chosen from C$_1$ to C$_6$ alkyl groups or phenyl groups;

C$_3$ to C$_{12}$ cycloalkyl groups such as isobornyl or cyclohexane,

C$_3$ to C$_{20}$ aryl groups such as phenyl,

C$_4$ to C$_{30}$ aralkyl groups (with a C1 to C8 alkyl group) such as 2-phenylethyl or benzyl, 4- to 12-membered heterocyclic groups comprising at least one heteroatom selected from O, N and S, the ring being aromatic or non-aromatic, and heterocycloalkyl groups a C$_1$ to C$_4$ alkyl group, such as furfurylmethyl or tetrahydrofurfurylmethyl;

(vi) styrene and its derivatives, for example, methylstyrene, chlorostyrene or chloromethylstyrene;

(vii) ethylenically unsaturated monomers comprising at least one silicon atoms, such as methacryloyloxypropyltrimethoxysiloxane and methacryloyloxypropyltris(trimethylsiloxy)silane;

and also their salts, and mixtures thereof.

Among these additional monomers non-limiting mention may be made of methyl, ethyl, n-propyl, isopropyl, n-butyl, t-butyl, cyclohexyl, methoxyethyl, ethoxyethyl, trifluoroethyl, dimethylaminoethyl, diethylaminoethyl, 2-hydroxypropyl and 2-hydroxyethyl (meth)acrylates; acrylic acid, methacrylic acid, (meth)acrylamide, methacryloyloxypropyltrimethoxy-silane, methacryloyloxypropyltris(trimethylsiloxy)silane; and also their salts; and mixtures thereof.

As additional monomers it is also possible to employ carbon or silicone macromonomers having at least one polymerizable end group. This is any polymer, for example, an oligomer, comprising at only one of its ends an end group, for example, a polymerizable end group, which during the polymerization reaction is capable of reacting with the monomers in question to form the side-chains of the polymer; said end group may, for example, be an ethylenically unsaturated group capable of undergoing free-radical polymerization with the monomers making up the skeleton. Said macromonomer allows the side-chains of the copolymer to be formed. The polymerizable group of the macromonomer may, for example, be an ethylenically unsaturated group capable of undergoing free-radical polymerization. Said polymerizable end group may, for example, be a vinyl or (meth)acrylate group. Among the additional macromonomers which can be employed non-limiting mention may be made, for example, of the following, alone or in a mixture, and also their salts:

(i) linear or branched C$_8$-C$_{22}$ alkyl (meth)acrylate homopolymers and copolymers having a polymerizable end group selected from vinyl or (meth)acrylate groups, among which non-limiting mention may be made of poly(2-ethylhexyl acrylate) macromonomers having a mono(meth)acrylate end group; poly(dodecyl acrylate) or poly(dodecyl methacrylate) macromonomers having a mono(meth)acrylate end group; and poly(stearyl acrylate) or poly(stearyl methacrylate) macromonomers having a mono(meth)acrylate end group. Macromonomers of this kind are described, for example, in European Patent Nos. EP895467 and EP96459.

(ii) polyolefins having an ethylenically unsaturated end group, for example, those having a (meth)acrylate end group. As examples of such polyolefins non-limiting mention may be made, for example, of the following macromonomers, on the understanding that they have a (meth)acrylate end group: polyethylene macromonomers, polypropylene macromonomers, polyethylene/polypropylene copolymer macromonomers, polyethylene/polybutylene copolymer macromonomers, polyisobutylene macromonomers; polybutadiene macromonomers; polyisoprene macromonomers; and poly(ethylene/butylene)-polyisoprene macromonomers. Macromonomers of this kind are described, for example, in U.S. Pat. No. 5,625,005, which mentions ethylene/butylene and ethylene/propylene macromonomers having a (meth)acrylate reactive end group. Non-limiting mention may be made, for example, of poly(ethylene/butylene) methacrylate, such as that sold under the name Kraton Liquid L-1253 by Kraton Polymers.

(iii) polydimethylsiloxanes having a mono(meth)acrylate end group, and for example, those of formula (IIa):

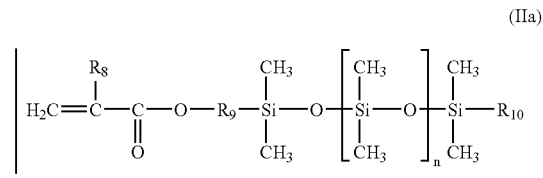

(IIa)

wherein:

R$_8$ is chosen from a hydrogen atom and a methyl group; for example, a methyl group;

R$_9$ is chosen from linear or branched, for example, linear, divalent hydrocarbon groups having 1 to 10 carbon atoms and optionally comprising one or two ether bonds —O—; for example, ethylene, propylene or butylene;

R$_{10}$ is chosen from a linear or branched alkyl groups having 1 to 10 carbon atoms, for example, 2 to 8 carbon atoms; for example, methyl, ethyl, propyl, butyl or pentyl;

n is chosen from an integer ranging from 1 to 300, for example, ranging from 3 to 200 and further, for example, ranging from 5 to 100.

As silicone macromonomers non-limiting mention may be made, for example, of monomethacryloyloxypropylpolydimethylsiloxanes, such as those sold under the name PS560-K6 by UCT (United Chemical Technologies Inc.) or under the name MCR-M17 by Gelest Inc.

Among the salts, non-limiting mention may be made of those obtained by neutralizing acid groups using mineral bases such as LiOH, NaOH, KOH, Ca(OH)$_2$, NH$_4$OH or Zn(OH)$_2$; or by an organic base such as a primary, secondary or tertiary alkylamine, for example, triethylamine or butylamine. This primary, secondary, or tertiary alkylamine may comprise at least one nitrogen and/or oxygen atoms and may therefore comprise, for example, at least one alcohol functions; non-limiting mention may be made, for example, of 2-amino-2-methylpropanol, triethanolamine and 2-dimethylaminopropanol. Non-limiting mention may also be made of lysine or 3-(dimethylamino)propylamine.

Non-limiting mention may also be made of the salts of mineral acids, such as sulphuric acid, hydrochloric acid, hydrobromic acid, hydriodic acid, phosphoric acid and boric acid. Non-limiting mention may also be made of the salts of organic acids, which may comprise at least one carboxylic, sulphonic or phosphoric acid groups. These may be linear, branched or cyclic aliphatic acids or else aromatic acids. These acids may further comprise at least one heteroatom selected from O and N, in the form for example of hydroxyl groups. Non-limiting mention may be made, for example, of propionic acid, acetic acid, terephthalic acid, citric acid and tartaric acid.

In one embodiment, the copolymer according to the disclosure comprises at least one "high-Tg" branch or polymeric sequence having a Tg greater than or equal to 20° C., for example, ranging from 20° C. to 150° C., further, for example, from 30° C. to 120° C., and even further, for example, from 40° C. to 100° C.

This branch is, for example, present in an amount greater than or equal to 50%, for example, from 55% to 95%, further, for example, from 60% to 90% by weight, relative to the total weight of the polymer.

Likewise, for example, the copolymer according to the disclosure comprises at least one "low-Tg" branch or sequence having a Tg of strictly lower than 20° C., for example, ranging from −150° C. to 19° C., further, for example, from −100° C. to 0° C., even further, for example, from −80° C. to −5° C., and even further, for example, from −70° C. to −10° C.

This branch is, for example, present in an amount less than 50%, for example, from 5% to 45%, further, for example, from 10% to 40% by weight, relative to the total weight of the polymer.

In another embodiment, the "high-Tg" branch comprises "high-Tg" monomers as defined below, which may be present in a proportion of 30% to 100% by weight, for example, 40% to 95% by weight, further, for example, from 50% to 90% by weight, relative to the total weight of said branch.

In another embodiment, the "low-Tg" branch comprises "low-Tg" monomers as defined below, which may be present in a proportion of 30% to 100% by weight, for example, 40% to 95% by weight, further, for example, from 50% to 90% by weight, relative to the total weight of said branch.

In another embodiment, copolymers are chosen such that the main branch is "high-Tg" and at least one of the secondary branches is "low-Tg".

Furthermore, the copolymers according to the disclosure, for example, comprise at least one "high-Tg" monomer having a Tg greater than or equal to 20° C., for example, ranging from 20 to 150° C., further, for example, ranging from 30 to 120° C., and even further, for example, from 40 to 100° C., or a mixture of such monomers.

The at least one "high-Tg" monomer may be selected from the monomers of choice and/or from the additional monomers as described above.

The "high-Tg" monomer or monomers may be present in a proportion of 40% to 100% by weight, for example, 50% to 80% by weight, further, for example, 55% to 70% by weight, relative to the total weight of monomers present in the copolymer.

In another embodiment, the copolymers according to the disclosure may therefore likewise comprise at least one "low-Tg" monomer having a Tg lower than than 20° C., for example, ranging from −150 to 19° C., further, for example, from −100 to 0° C., even further, ranging from −80 to −5° C., and even further, for example, from −70° C. to −10° C., or a mixture of such monomers, said monomer or monomers being present in a proportion of 0 to 60% by weight, for example, from 20% to 50% by weight, further, for example, from 30% to 45% by weight, relative to the total weight of monomers present in the copolymer.

The at least one "low-Tg" monomer may be selected from the monomers of choice and/or from the additional monomers as described above.

By way of information it is noted that isobornyl acrylate has a Tg of 94° C., isobornyl methacrylate a Tg of 110° C., and isobutyl methacrylate a Tg of 53° C., and they are all therefore "high-Tg" monomers, with a Tg of more than 20° C., whereas isobutyl acrylate has a Tg of −24° C. and 2-ethylhexyl acrylate has a Tg of −50° C., and they are therefore "low-Tg" monomers, with a Tg less than 20° C.

As used herein, "Tg monomer" means those monomers whose homopolymer has such a Tg. In the present disclosure the Tg (or glass transition temperatures) are theoretical Tg determined from the theoretical Tg of the constituent monomers of each of the sequences, and may be found in a reference manual such as the Polymer Handbook, 3rd ed. 1989, John Wiley, in accordance with the following relationship, known as Fox's law:

$$\frac{1}{Tg} = \sum_i \left(\frac{\varpi i}{Tgi}\right)$$

$\omega_i$ being the mass fraction of the monomer i in the sequence in question and Tgi being the glass transition temperature of the homopolymer of the monomer i (in kelvins).

In another embodiment, the copolymer according to the disclosure comprises at least one lipophilic monomer, which may be selected from the monomers of choice and/or from the additional monomers, and which may be present in a proportion of 40% to 100% by weight, for example, 50% to 80% by weight, further, for example, 55% to 70% by weight, relative to the total weight of monomers present in the copolymer.

In another embodiment, the copolymer according to the disclosure may comprise at least one hydrophilic monomers, which may be selected from the monomers of choice and/or from the additional monomers and which may be present in a proportion of 0 to 60% by weight, for example, 20% to 50% by weight, further, for example, 30% to 45% by weight, relative to the total weight of monomers present in the copolymer.

The copolymer according to the disclosure, for example, comprises 100% by weight of lipophilic monomers, which may be selected from the monomers of choice and/or from the additional monomers.

In another embodiment, the copolymer according to the disclosure is chosen from copolymers wherein the main branch is lipophilic, and in a further embodiment a copolymer wherein the entirety of the branches, both main and secondary, are lipophilic.

By way of information it will be noted that isobornyl acrylate, isobornyl methacrylate, isobutyl methacrylate, isobutyl acrylate and 2-ethylhexyl acrylate are lipophilic.

As used herein, a lipophilic monomer means any non-hydrophilic monomer.

As used herein, a hydrophilic monomer means any monomer whose homopolymer is water-soluble, i.e. does not form a precipitate, but instead forms, for example, a clear solution, in water, at 25° C., at 1 atm and at a concentration of at least 1% by weight.

The skilled person will be able to select the monomers and their amounts as a function of the desired result, based on his or her general knowledge, for example, on the relative reactivity of each monomer, on its Tg and on its lipophilicity. For example, he or she will select the monomers and their amount, and also the solvent medium, so as to give a copolymer which is soluble in said solvent medium.

In one embodiment, when the copolymer according to the disclosure comprises acrylic acid and/or methacrylic acid, said monomers, for example, may be present in a maximum amount of 20% by weight, for example, an amount less than 15% by weight, for example, less than 10% by weight, relative to the total weight of monomers present in the copolymer, so as to preserve its lipophilicity to the final copolymer.

In an embodiment, the number-average molecular mass of the copolymer according to the disclosure ranges from 2000 g/mol to 1500000 g/mol, for example, from 5500 g/mol to 1000000 g/mol, and further, for example, from 6000 g/mol to 900000 g/mol.

The weight-average (Mw) and number-average (Mn) molecular masses are determined by liquid gel-permeation chromatography (GPC), with THF as eluent, a calibration curve drawn up with linear polystyrene standards, and a refractometric detector.

The hyperbranched copolymers according to the disclosure may be obtained from polymerization processes which are themselves known to the person skilled in the art.

Non-limiting mention may be made of a process comprising at least one step comprising a free-radical polymerization in the presence of a polyfunctional compound.

Thus it is possible to react:
the ethylenic monomer or monomers envisaged for forming the copolymer, or, for example, some of them, namely the monomer or monomers of choice and/or additional monomer or monomers, as defined above; and
at least one polyfunctional compound, i.e. a compound comprising at least two polymerizable functional groups or unsaturations, this compound also being called a "chain extender" and defined below.

The reaction can be performed in two steps, the first step comprising copolymerizing the monomers envisaged for forming the main branch, in the presence of a small amount of polyfunctional compound; for example, the reactivity of the functional groups of said polyfunctional compound is such that the monomers envisaged for forming the main branch will react preferentially with a first functional group, leaving at least one of the other functional groups unreacted.

In a second step, the monomers capable of forming the other branches can be added, and will react preferentially with the unreacted functional group of the polyfunctional compound, so as to form the hyperbranched copolymer. In this second step it is possible to add further polyfunctional compound.

For example, the functions of the polyfunctional compound exhibit different reactivities. For example, the polyfunctional compound may comprise a (meth)acrylate function, which will polymerize rapidly, and an allylic function, which will polymerize more slowly.

As an example of a polyfunctional compound non-limiting mention may be made, for example, of the compounds of formula (I) below:

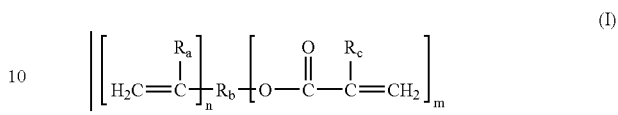

wherein:
$R_a$ and $R_c$, which may be identical or different, each are chosen from hydrogen and linear or branched alkyl radicals having 1 to 22 carbon atoms, for example, 1 to 3 carbon atoms; for example, $R_a$ may be a hydrogen atom; for example, $R_c$ may be a methyl radical;
$R_b$ is chosen from linear or branched divalent alkylene groups having 1 to 22 carbon atoms, divalent cycloalkylene groups having 3 to 6 carbon atoms, divalent arylene groups having 6 to 18 carbon atoms, and divalent alkarylene group having 7 to 24 carbon atoms; for example, $R_b$ is a methylene group;
m and n independently of one another are 1, 2, 3 or 4 and are such that the sum m+n is greater than or equal to 2; for example, m=n=1.

A polyfunctional compound or chain extender may, for example, be chosen from allyl (meth)acrylates, for example, allyl methacrylate.

Said polyfunctional compound may be used in an amount 0.05% to 15% by weight, for example, from 0.1% to 10% by weight, further for example, from 0.5% to 5% by weight of compound relative to the total weight of the final copolymer.

Dislcosed herein is a copolymer obtainable by a process comprising:
a first step comprising the free-radical polymerization in the presence of at least one polyfunctional compound comprising at least two polymerizable functional groups, some of the monomers envisaged, selected from the monomer or monomers of choice and/or the additional monomer or monomers, as defined above; and
a second step comprising the free-radical polymerization of the envisaged monomers, selected from the monomer or monomers of choice and/or the additional monomer or monomers, as defined above, optionally in the presence of a polyfunctional compound.

Hyperbranched copolymers may also be synthesized by reacting:
the free-radically polymerizable ethylenic monomer or monomers envisaged, and
compounds comprising at least one unsaturation and at least one site capable of initiating the polymerization, following activation by temperature, by UV radiation or by any mechanism other than that of polymerization of the unsaturation; these compounds therefore comprise both a site capable of promoting chain propagation, i.e. a site comprising a double bond, and a site A capable of initiating the chains.

This method is called "self-condensing vinyl polymerization". It is described in the work "Chimie et physico-chimie des polymères" M. Fontanille, Y. Gnanou (publ. Dunod) 2002, page 368.

To form hyperbranched polymers the unsaturations and/or the site A capable of initiating the chains may be capable of reacting according to a mechanism of controlled free-radical polymerization, for example, according to a process of atom-transfer radical polymerization (ATRP), described, for example, in Macromolecules 2002, 35, pp. 1146-48, Jho J Y and Yoo S H; or else in Polym. Prepr. 1996, 37(2), 413-14; or else Matyjaszewski "Progress in polymer science" 26 (3), 337-77, 2001, Annex 2.2; Chem. review 2001, 101/12, 3737; Mueller "Macromolecules" 34/18, 62026-13, 2001.

Generally speaking, atom-transfer free-radical polymerization takes place by polymerization of at least one free-radically polymerizable monomers in the presence:

of an initiator having at least one transferable halogen atom,
of a compound comprising a transition metal capable of participating in a reduction step with the initiator and a "dormant" polymeric chain;
and of a ligand selectable from compounds comprising a nitrogen (N), oxygen (O), phosphorus (P) or sulphur (S) atom and capable of undergoing coordination via a bond to said compound comprising a transition metal.

This process is described, for example, in PCT Application No. WO 97/18247 and in the article by Matyjasezwski et al. published in *JACS,* 117, page 5641 (1995). The halogen atom is, for example, a chlorine or bromine atom.

In this case, the site A capable of initiating the chains will be able to be, for example, R1-Cl, with R1 chosen from benzene and OCOCH(CH$_3$)—.

Among the other processes which can be used non-limiting mention may be made of the nitroxides method, described for example in *Chem. review* 2001, 101(12), p. 3681. The technique of free-radical polymerization by reaction with a nitroxide consists in blocking the growing free-radical species in the form of a bond of type C—O NR1R2, wherein R1 and R2, which may be identical or different, are each chosen from alkyl radicals having 2 to 30 carbon atoms, or together forming, with the nitrogen atom, a ring having 4 to 20 carbon atoms, such as a 2,2,6,6-tetramethylpiperidinyl ring, for example.

This polymerization technique is described, for example, in the articles "Synthesis of nitroxy-functionalized polybutadiene by anionic polymerization using a nitroxy-functionalized terminator", published in *Macromolecules* 1997, volume 30, pp. 4238-42, and "Macromolecular engineering via living free radical polymerizations", published in *Macromol. Chem. Phys.* 1998, vol. 199, pp. 923-35, or else in PCT Application No. WO-A-99/03894.

In this case, the site A capable of initiating the chains will be able to be, for example, of formula:

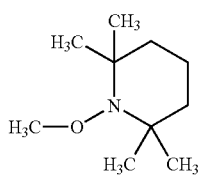

It is also possible to employ the anionic polymerization method described for example in Chem. Review 2001, 101/12, p. 3787, and also the cationic polymerization method described for example by Charleux et al. in Advances in Polymer Science 142, pp. 1-69, 1999.

The copolymers according to the disclosure have the advantage of being readily employable in organic cosmetic media, for example, those of oily or lipophilic solvent type, while retaining advantageous rheological properties.

The copolymers may be present in the cosmetic or pharmaceutical compositions, for example, topical dermatological compositions, in an amount of 0.1% to 95% by weight, for example, 0.5% to 90% by weight, for example, 1% to 80% by weight, for example, 5%-70% by weight, relative to the total weight of the composition.

The copolymers may be present in the composition in dissolved form, for example in a cosmetic organic solvent or a cosmetic oil. Indeed it has been noted that the copolymers according to the disclosure may be soluble therein and that they can be employed therein while retaining advantageous rheological properties.

The cosmetic or pharmaceutical compositions, for example, dermatological compositions, according to the disclosure comprise, in addition to said copolymers, a physiologically acceptable medium, for example, a cosmetically or dermatologically acceptable medium, in other words a medium which is compatible with keratin materials such as the skin of the face or body, lips, hair, eyelashes, eyebrows and nails.

The composition may, for example, comprise a solvent medium, which may be a fatty phase, which may itself comprise oils and/or solvents, which are, for example, lipophilic, and also fatty substances which are solid at ambient temperature, such as waxes, pasty fatty substances, gums, and also mixtures thereof.

Among the constituents of the fatty phase, non-limiting mention may be made of oils and/or solvents having an overall solubility parameter according to the Hansen solubility space of less than or equal to 20 (MPa)$^{1/2}$, for example, less than or equal to 18 (MPa)$^{1/2}$, further, for example, less than or equal to 17 (MPa)$^{1/2}$.

The overall solubility parameter δ according to the Hansen solubility space is defined in the article "Solubility parameter values" by Eric Grulke in the work "Polymer Handbook", 3rd edition, chapter VII, pp. 519-59 by the following relationship:

$$\delta = (dD^2 + dP^2 + dH^2)^{1/2}$$

wherein:
dD characterizes the London dispersion forces resulting from the formation of dipoles induced during molecular impacts,
dP characterizes the Debye interaction forces between permanent dipoles, and
dH characterizes the specific interaction forces (of hydrogen bond, acid/base, donor/acceptor type, etc.).

The definition of solvents in the Hansen solubility space is described in the article by C. M. Hansen "The three dimensional solubility parameters", J. Paint Technol. 39, 105 (1967).

Among oils and/or solvents having an overall solubility parameter according to the Hansen solubility space of less than or equal to 20 (MPa)$^{1/2}$, non-limiting mention may be made of oils, volatile or non-volatile, which may be selected from natural or synthetic, carbon, hydrocarbon and fluoro oils, optionally branched, alone or in a mixture; ethers and esters having more than 6 carbon atoms, for example, 6 to 30 carbon atoms; ketones having more than 6 carbon atoms, for example, 6 to 30 carbon atoms; and aliphatic fatty monoalcohols having 6 to 30 carbon atoms, the hydrocarbon chain comprising no substituent group.

As used herein, "non-volatile oil" means an oil capable of remaining on the skin at ambient temperature and atmospheric pressure for at least one hour and for example, having a non-zero vapour pressure, at ambient temperature (25° C.) and atmospheric pressure, of less than 0.01 mmHg (1.33 Pa).

Non-limiting mention may be made, for example, of non-volatile carbon oils, for example, hydrocarbon oils, of plant, mineral, animal or synthetic origin, such as liquid paraffin (or vaseline), squalane, hydrogenated polyisobutylene (Parleam oil), perhydrosqualene, mink oil, macadamia oil, turtle oil, soya oil, sweet almond oil, calophyllum oil, palm oil, grapeseed oil, sesame oil, corn oil, arara oil, rapeseed oil, sunflower oil, cottonseed oil, apricot oil, castor oil, avocado oil, jojoba oil, olive oil or cereal germ oil, or karite butter; linear, branched or cyclic esters having more than 6 carbon atoms, for example, 6 to 30 carbon atoms, such as esters of lanolic acid, of oleic acid, of lauric acid and of stearic acid; esters derived from long-chain alcohols or acids (i.e. those having 6 to 20 carbon atoms), for example, the esters of formula RCOOR' wherein R is chosen from the residue of a higher fatty acid comprising 7 to 19 carbon atoms and R' is chosen from a hydrocarbon chain comprising 3 to 20 carbon atoms, for example, $C_{12}$-$C_{36}$ esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, di(2-ethylhexyl) succinate, diisostearyl malate, glycerol triisostearate or diglycerol triisostearate; higher fatty acids, for example, $C_{14}$-$C_{22}$ acids, such as myristic acid, palmitic acid, stearic acid, behenic acid, oleic acid, linoleic acid, linolenic acid or isostearic acid; higher fatty alcohols, for example, $C_{16}$-$C_{22}$ alcohols, such as cetanol, oleyl alcohol, linoleyl alcohol or linolenyl alcohol, isostearyl alcohol or octyldodecanol; and mixtures thereof.

Non-limiting mention may also be made of decanol, dodecanol, octadecanol, the liquid triglycerides of fatty acids of 4 to 10 carbon atoms, such as the triglycerides of heptanoic or octanoic acid, the triglycerides of caprylic/capric acids; linear or branched hydrocarbons of mineral or synthetic origin, such as liquid paraffins and derivatives thereof, vaseline, polydecenes, hydrogenated polyisobutene such as Parleam; synthetic esters and ethers, for example, those of fatty acids, such as, for example, Purcellin oil, isopropyl myristate, 2-ethylhexyl palmitate, 2-octyldodecyl stearate, 2-octyldodecyl erucate, isostearyl isostearate; hydroxy esters such as isostearyl lactate, octyl hydroxystearate, octyldodecyl hydroxystearate, diisostearyl malate, triisocetyl citrate, and heptanoates, octanoates and decanoates of fatty alcohols; polyol esters such as propylene glycol dioctanoate, neopentyl glycol diheptanoate, diethylene glycol diisononanoate; and esters of pentaerythritol; fatty alcohols having 12 to 26 carbon atoms such as octyldodecanol, 2-butyloctanol, 2-hexyldecanol and 2-undecylpentadecanol.

Non-limiting mention may also be made of ketones which are liquid at ambient temperature, such as methyl ethyl ketone, methyl isobutyl ketone, diisobutyl ketone, isophorone, cyclohexanone and acetone; propylene glycol ethers which are liquid at ambient temperature, such as propylene glycol monomethyl ether, propylene glycol monomethyl ether acetate, and dipropylene glycol mono-n-butyl ether; short-chain esters (having 3 to 8 carbon atoms in total) such as ethyl acetate, methyl acetate, propyl acetate, n-butyl acetate, and isopentyl acetate; ethers which are liquid at ambient temperature, such as diethyl ether, dimethyl ether or dichlorodiethyl ether; alkanes which are liquid at ambient temperature, such as decane, heptane, dodecane, isododecane, isohexadecane and cyclohexane; cyclic aromatic compounds which are liquid at ambient temperature, such as toluene and xylene; aldehydes which are liquid at ambient temperature, such as benzaldehyde and acetaldehyde, and mixtures thereof.

Among the volatile compounds non-limiting mention may be made of volatile non-silicone oils, for example, $C_8$-$C_{16}$ isoparaffins such as isododecane, isodecane, isohexadecane and, for example, the oils sold under the trade names Isopar and Permethyl, and for example, isododecane (Permethyl 99 A).

Non-limiting mention may be made of volatile or non-volatile alkanes which are liquid at ambient temperature, and, for example, decane, heptane, dodecane, isododecane, isohexadecane, cyclohexane, isodecane, and mixtures thereof.

These oils and/or solvents may be present in an amount ranging from 0.01% to 95%, for example, from 0.1% to 90%, further, for example, from 10% to 85% by weight, relative to the total weight of the composition, and even further, for example, from 30% to 80%.

The composition may further comprise a hydrophilic medium comprising water or a mixture of water and at least one hydrophilic organic solvents such as alcohols, and for example, lower linear or branched monoalcohols having 2 to 5 carbon atoms such as ethanol, isopropanol or n-propanol, and polyols such as glycerol, diglycerol, propylene glycol, sorbitol, pentylene glycol, and polyethylene glycols, or else hydrophilic $C_2$-$C_4$ aldehydes and $C_2$ ethers.

The water or mixture of water and hydrophilic organic solvents may be present in the composition according to the disclosure in an amount ranging from 0.1% to 80% by weight, relative to the total weight of the composition, and, for example, from 1% to 70% by weight.

The composition according to the disclosure may also comprise waxes and/or gums.

As used herein, "wax" means a lipophilic compound which is solid at ambient temperature (25° C.), exhibits a reversible solid/liquid state change, and has a melting point which is greater than or equal to 30° C. and may range up to 120° C. By converting the wax to the liquid state (melting) it is possible to make it miscible with the oils that are optionally present and to form a microscopically homogeneous mixture, but by taking the temperature of the mixture to ambient temperature the wax recrystallizes in the oils of the mixture. The melting point of the wax may be measured by means of a differential scanning calorimeter (DSC), for example the calorimeter sold under the name DSC 30 by Mettler.

The waxes may be hydrocarbon, fluoro and/or silicone waxes and may be plant, mineral, animal and/or synthetic in origin. For example, the waxes may exhibit a melting temperature greater than 25° C., for example, greater than 45° C. As a wax which can be used in the composition of the disclosure non-limiting mention may be made of beeswax, carnauba wax or candelilla wax, paraffin, microcrystalline waxes, ceresin or ozokerite, synthetic waxes such as polyethylene waxes or Fischer-Tropsch waxes, and silicone waxes such as alkyl- or alkoxy-dimethicones having 16 to 45 carbon atoms.

The gums may be polydimethylsiloxanes (PDMS) of high molecular weight or cellulose gums or polysaccharides, and the pasty substances may be hydrocarbon compounds such as lanolins and derivatives thereof or else PDMS.

The nature and amount of the solids are a function of the desired mechanical properties and textures. By way of indication, the composition may comprise from 0.01% to 50% by weight of waxes, relative to the total weight of the composition, for example, from 1% to 30% by weight.

The composition according to the disclosure may further comprise at least one colorant selected from water-soluble dyes, fat-soluble dyes, and pulverulent colorants such as pigments, nacres and flakes which are well known to the skilled person. Within the composition the colorants may be present in an amount ranging from 0.01% to 50% by weight, relative to the weight of the composition, for example, from 0.01% to 30% by weight.

By pigments are meant mineral or organic, white or colored particles of any shape which are insoluble in the physiological medium and are intended for coloring the composition. By nacres are meant iridescent particles of any shape, for example, those produced by certain molluscs in their shell, or else synthesized. The pigments may be white or colored, mineral and/or organic. Among mineral pigments non-limiting mention may be made of titanium dioxide, optionally surface-treated, zirconium oxide or cerium oxide, and also zinc oxide, iron oxides (black, yellow or red) or chromium oxide, manganese violet, ultramarine blue, chromium hydrate and ferric blue, and metal powders such as aluminium powder and copper powder. Among organic pigments non-limiting mention may be made of carbon black, D & C pigments, and lakes based on cochineal carmine, barium, strontium, calcium or aluminium. The nacreous pigments may be selected from white nacreous pigments such as titanium-coated mica or bismuth oxychloride, colored nacreous pigments such as titanium mica coated with iron oxides, titanium mica coated with, for example, ferric blue or chromium oxide, titanium mica coated with an organic pigment of the aforementioned type, and nacreous pigments based on bismuth oxychloride.

Among water-soluble dyes non-limiting mention may be made of the disodium salt of ponceau, the disodium salt of alizarin green, quinoline yellow, the trisodium. salt of amaranth, the disodium salt of tartrazine, the monosodium salt of rhodamine, the disodium salt of fuchsin, xanthophyll and methylene blue.

The composition according to the disclosure may further comprise at least one filler, for example, in an amount ranging from 0.01% to 50% by weight, relative to the total weight of the composition, for example, ranging from 0.01% to 30% by weight. By fillers are meant particles of any shape, colorless or white, mineral or synthetic, which are insoluble in the medium of the composition irrespective of the temperature at which the composition is manufactured. These fillers serve, for example, to modify the rheology or texture of the composition. The fillers may be mineral or organic and of any shape—platelet-like, spherical or oblong, irrespective of the crystallographic form (for example sheet, cubic, hexagonal, orthorhombic, etc.). Non-limiting mention may be made of talc, mica, silica, kaolin, polyamide (Nylon®) powders (Orgasol® from Atochem), poly-β-alanine powder and polyethylene powder, powders of tetrafluoroethylene polymers (Teflon®), lauroyllysine, starch, boron nitride, hollow polymeric microspheres such as those of polyvinylidene chloride/acrylonitrile, for instance Expancel® (Nobel Industries) and of acrylic acid copolymers (Polytrap® from Dow Corning), and silicone resin microbeads (Tospearls® from Toshiba, for example), particles of elastomeric polyorganosiloxanes, precipitated calcium carbonate, magnesium carbonate and hydrogen carbonate, hydroxyapatite, hollow silica microspheres (Silica Beads® from Maprecos), glass or ceramic microcapsules, metal soaps derived from organic carboxylic acids having 8 to 22 carbon atoms, for example, 12 to 18 carbon atoms, for example zinc stearate, magnesium stearate or lithium stearate, zinc laurate or magnesium myristate.

The composition may further comprise an additional polymer such as a film-forming polymer. As used herein, "film-forming polymer" means a polymer capable of forming, by itself or in the presence of a film-forming auxiliary, a continuous film which adheres to a substrate, for example, to keratin materials. Among the film-forming polymers which can be used in the composition of the present disclosure non-limiting mention may be made of synthetic polymers, of free-radical or polycondensate type, polymers of natural origin, and mixtures thereof, for example, acrylic polymers, polyurethanes, polyesters, polyamides, polyureas and cellulosic polymers such as nitrocellulose.

The composition according to the disclosure may also comprise ingredients commonly used in cosmetology, such as vitamins, thickeners, gelling agents, trace elements, softeners, sequestrants, perfumes, alkalifying or acidifying agents, preservatives, sunscreens, surfactants, antioxidants, anti-hair-loss agents, anti-dandruff agents, propellants, ceramides, or mixtures thereof. It will be appreciated that the person skilled in the art will take care to select this or these optional complementary compounds, and/or their amount, in such as way that the advantageous properties of the composition according to the disclosure are not, or not substantially, adversely affected by the addition envisaged.

The composition according to the disclosure may take the form, for example, of a suspension, a dispersion, a solution, for example, an organic solution, a gel, an emulsion, for example, an oil-in-water (O/W) or water-in-oil (W/O) emulsion or multiple (W/O/W or polyol/O/W or O/W/O) emulsion, or the form of a cream, a paste, a mousse, a vesicle dispersion, for example, of ionic or nonionic lipids, a two-phase or multi-phase lotion, a spray, a powder, a paste, for example, a flexible paste (in particular a paste having a dynamic viscosity at 25° C. of the order of 0.1 to 40 Pa·s at a shear rate of 200 s$^{-1}$, after 10 minutes of measurement in cone/plate geometry). The composition may be anhydrous: it may be an anhydrous paste.

The skilled person will be able to select the appropriate presentation form, and the method of preparing it, on the basis of his or her general knowledge, taking into account on the one hand the nature of the constituents used, and for example, their solubility in the vehicle, and on the other hand the application envisaged for the composition.

The composition according to the disclosure may be a makeup composition, for example, a complexion product such as a foundation, blusher or eyeshadow; a lip product such as a lipstick or lip care product; a concealer product; a blusher, mascara or eyeliner; an eyebrow makeup product, a lip pencil or eye pencil; a product for the nails such as a nail varnish or nail care product; a body makeup product; or a hair makeup product (mascara or lacquer for hair).

The composition according to the disclosure may be a composition for protecting or caring for the skin of the face, neck, hands or body, for example, an anti-Wrinkle composition or anti-fatigue composition allowing a glow to be imparted to the skin, or a moisturizing or treatment composition; or an anti-sun or artificial tanning composition.

The composition according to the disclosure may also be a hair product, for example, for holding the hairstyle or shaping the hair. Hair compositions are, for example, shampoos, gels, setting lotions, styling lotions, fixing compositions and styling compositions such a lacquers or sprays. The lotions may be packaged in various forms, for example, in spray dispensers, pump flasks or aerosol containers, so as to provide for application of the composition in vaporized form or in foam form. Packaging forms of this kind are indicated, for example, when the desire is to obtain a spray or a mousse for fixing or treating the hair.

For example, the composition according to the disclosure may be a makeup composition, for example, a foundation or a lipstick.

Disclosed herein is a cosmetic method of making up or caring for keratin materials, for example, the skin of the body or the face, the lips, the nails, the hair and/or the eyelashes, comprising applying to said materials a cosmetic composition as defined above.

Disclosed herein is a cosmetic method of making up the skin of the face and/or the lips, comprising applying to said materials a cosmetic foundation or lipstick composition as defined above.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contain certain errors necessarily resulting from the standard deviation found in their respective testing measurements.

The embodiments disclosed herein are illustrated in greater detail by the examples described below.

Method of Determining the Dynamic Storage Modulus E'

The dynamic storage modulus E' is determined by DMTA (Dynamic and Mechanical Temperature Analysis).

To measure E', viscoelasticimetry tests are performed using a DMTA instrument from TA Instruments (model DMA2980) on a polymer film sample approximately 250±50 µm thick, 5 mm wide and 10 mm long, after drying at 23° C. and 50-55% relative humidity for 4 days. This sample is subjected to a tensile stress. The sample undergoes a weak static force ($\cong 0.1$ N) superposed on which there is a sinusoidal displacement of ±8 µm at the frequency of 1 Hz. Hence operation takes place in the linear field, at low levels of deformation. This tensile stress is carried out on the sample at temperatures varying from −150° C. to +200° C., with a temperature change of 3° C. per minute.

Using the DMA, a measurement is then made of the complex modulus $E^* = E' + iE$ of the polymer tested (where E' is chosen from the dynamic storage modulus and E is chosen from the dynamic loss modulus).

The value of the complex modulus at 22° C. is used to deduce the dynamic storage modulus E' at a frequency of 1 Hz.

EXAMPLE 1

A 500-ml reactor with central stirring, nitrogen inlet, thermometer and condenser was charged with 75 g of heptane and heated to 90° C.

The following were then introduced:

feed stream 1: 35 g of isobornyl acrylate, 34 g of isobornyl methacrylate and 1 g of allyl methacrylate, over 1 hour;

feedstream 2: 1 g of Trigonox 21S and 25 g of heptane, over 48 hours.

When feedstream 1 had finished, feedstream 3 was introduced, comprising 30 g of 2-ethylhexyl acrylate, over 2 hours.

Heating was maintained constantly at 90° C. After the end of feedstream 2 the system was left at the reflux of the solvent for 3 hours.

120 g of isododecane were added and then the heptane was distilled off under reduced pressure to give a solution of the polymer in isododecane with a solids content of 51%.

Glass transition temperature: 10° C.

Measurement of the modulus E'=64±3 MPa

EXAMPLE 2

An anhydrous foundation was prepared, comprising (% by weight):

| | |
|---|---|
| polyethylene wax | 12% |
| volatile silicone oils | 25% |
| phenyl trimethicone | 20% |
| polymethyl methacrylate microspheres | 12% |
| solution of the polymer from Example 1 at 51% solids in isododecane | 12% |
| isododecane | qs 100% |

The waxes were melted and then, when the whole is clear, the phenyl trimethicone was added with stirring, and the silicone oils; thereafter the microspheres, isododecane and polymer were added. The mixture was homogenized for 15 minutes and then the resulting composition was cast and left to cool. This gave an anhydrous foundation.

EXAMPLE 3

A lipstick was prepared, comprising:

| | |
|---|---|
| polyethylene wax | 15% |
| solution of the polymer from Example 1 at 51% solids in isododecane | 20% |
| hydrogenated polyisobutene (Parleam from Nippon Oil Fats) | 25% |
| pigments | 10% |
| isododecane | qs 100% |

The composition obtained following application to the lips exhibited good cosmetic properties.

EXAMPLE 4

A foundation composition was prepared, comprising (% by weight):

| | |
|---|---|
| Phase A | |
| cetyl dimethicone copolyol (Abil EM 90 from Goldschmidt) | 3 g |
| isostearyl diglyceryl succinate (Imwitor 780K from Condea) | 0.6 g |
| pigments (iron oxides and titanium oxide) | 10 g |
| polyamide powder (Nylon-12) | 8 g |
| solution of the polymer from Example 1 at 51% solids in isododecane | 17 g |
| perfume | qs |
| isododecane | 10 g |
| Phase B | |
| magnesium sulphate | 0.7 g |
| preservative | qs |
| water | qs 100 g |

The composition obtained exhibited good cosmetic properties.

What is claimed is:

1. A hyperbranched copolymer comprising at least two polymeric branches, which may be identical or different, each comprising at least one at least trifunctional branch point, wherein a first polymeric branch comprises at least one first monomer chosen from isobornyl acrylate and isobornyl methacrylate, and a second polymeric branch comprises at least one second monomer chosen from isobornyl acrylate, isobornyl methacrylate, isobutyl acrylate, isobutyl methacrylate and 2-ethylhexyl acrylate.

2. A hyperbranched copolymer according to claim 1, wherein the at least two polymeric branches are connected to one another by a polyfunctional compound comprising at least two polymerizable functional groups.

3. A hyperbranched copolymer according to claim 2, wherein the polyfunctional compound is chosen from compounds of formula (I):

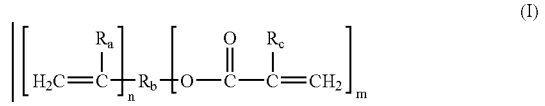

wherein:
- $R_a$ and $R_c$, which may be identical or different, are each chosen from hydrogen and linear or branched alkyl radicals having 1 to 22 carbon atoms;
- $R_b$ is chosen from linear or branched divalent alkylene groups having 1 to 22 carbon atoms, divalent cycloalkylene groups having 3 to 6 carbon atoms, divalent arylene groups having 6 to 18 carbon atoms, and divalent alkarylene groups having 7 to 24 carbon atoms;
- m and n, which may be identical or different, are each chosen from 1, 2, 3 or 4.

4. A hyperbranched copolymer according to claim 3, wherein $R_a$ is a hydrogen atom.

5. A hyperbranched copolymer according to claim 3, wherein $R_c$ is a methyl radical.

6. A hyperbranched copolymer according to claim 3, wherein $R_b$ is a methylene group.

7. A hyperbranched copolymer according to claim 3, wherein the polyfunctional compound is chosen from allyl (meth)acrylates.

8. A hyperbranched copolymer according to claim 1, wherein each polymeric branch is in the form of a polymeric sequence of homopolymer type or of random, alternating, block or gradient copolymer type.

9. A hyperbranched copolymer according to claim 1, wherein each polymeric branch is in the form of a linear random copolymer or homopolymer.

10. A hyperbranched copolymer according to claim 1, wherein the main branch is in the form of a homopolymer or a random copolymer comprising 80% to 100% by weight, relative to the weight of the main branch, of at least one monomer chosen from isobornyl acrylate and isobornyl methacrylate; and/or the secondary branch is in the form of a homopolymer or a random copolymer comprising 80% to 100% by weight relative to the weight of the branch, of at least one monomer chosen from isobornyl acrylate, isobornyl methacrylate, isobutyl acrylate, isobutyl methacrylate and 2-ethylexyl acrylate.

11. A hyperbranched copolymer according to claim 1, wherein the total amount in the hyperbranched copolymer, of monomers chosen from isobornyl acrylate, isobornyl methacrylate, isobutyl acrylate, isobutyl methacrylate and 2-ethylexyl acrylate ranges from 50% to 100% by weight relative to the total weight of monomers present in the hyperbranched copolymer.

12. A hyperbranched copolymer according to claim 1, comprising 25% to 75% by weight of the first monomer, with is present in the first branch, and 25% to 75% by weight of the second monomer, with may be present in the same branch or in another branch, wherein the percentages are relative to the total weight of monomers present in the hyperbranched copolymer.

13. A hyperbranched copolymer according to claim 1, comprising a third monomer chosen from isobornyl acrylate, isobornyl methacrylate, isobutyl acrylate, isobutyl methacrylate and 2-ethylexyl acrylate present in an amount ranging from 1% to 40% by weight relative to the weight of the hyperbranched copolymer.

14. A hyperbranched copolymer according to claim 1, comprising, in the same branch or in different branches, the monomer combinations chosen from:
- isobornyl acrylate and isobornyl methacrylate;
- isobornyl acrylate and isobutyl acrylate;
- isobornyl acrylate and isobutyl methacrylate;
- isobornyl acrylate and 2-ethylexyl acrylate;
- isobornyl methacrylate and isobutyl acrylate;
- isobornyl methacrylate and isobutyl methacrylate;
- isobornyl methacrylate and 2-ethylhexyl acrylate;
- isobornyl acrylate, isobornyl methacrylate and 2-ethylhexyl acrylate;
- isobornyl acrylate, isobornyl methacrylate and isobutyl acrylate;
- isobornyl acrylate, isobutyl methacrylate and 2-ethylhexyl acrylate;
- isobornyl acrylate, isobutyl methacrylate and isobutyl acrylate; and
- isobornyl methacrylate, isobutyl methacrylate and isobutyl acrylate.

15. A hyperbranched copolymer according to claim 1, comprising monomer combinations chosen from:
- isobornyl acrylate in the main branches and isobutyl acrylate in the secondary branches;
- isobornyl acrylate in the main branches and 2-ethylhexyl acrylate in the secondary branches;
- isobornyl methacrylate in the main branches and isobutyl acrylate in the secondary branches;
- isobornyl methacrylate in the main branches and 2-ethylhexyl acrylate in the secondary branches;
- isobornyl acrylate and isobornyl methacrylate in the main branches and isobutyl acrylate in the secondary branches;
- isobornyl acrylate and isobornyl methacrylate in the main branches and 2-ethylhexyl acrylate in the secondary branches;
- isobornyl acrylate and isobutyl methacrylate in the main branches and isobutyl acrylate in the secondary branches; and
- isobornyl acrylate and isobutyl methacrylate in the main branches and 2-ethylexyl acrylate in the secondary branches.

16. A hyperbranched copolymer according to claim 1, further comprising at least one additional monomer, which may be present in an amount ranging from 0% to 50% by weight, relative to the total weight of monomers present in the hyperbranched copolymer.

17. A hyperbranched copolymer according to claim 16, wherein the at least one additional monomer is chosen from the following monomers, and the salts thereof:
(meth)acrylates of formula $CH_2$=CHCOOR or $CH_2$=C($CH_3$)COOR wherein R is chosen from:
- a linear or branched alkyl groups comprising from 1 to 30 carbon atoms, wherein said alkyl is intercalated with at least one heteroatom selected from O, N, S and P, and/or wherein said alkyl group is optionally substituted by at least one substituent selected from
OH,
halogen atoms,
NR4R5, wherein R4 and R5, which may be identical or different, are chosen from hydrogen, $C_1$ to $C_6$ linear or branched alkyl groups, and phenyl groups; and
polyoxyalkylene groups comprising the repetition of 5 to 30 oxyalkylene units;
a $C_3$ to $C_{12}$ cycloalkyl group, said cycloalkyl group being able to contain, in its chain, at least one heteroatom chosen from O, N, S and P, and/or to be optionally substituted by at least one substituent selected from —OH and halogen atoms; and
a $C_4$ to $C_{20}$ aryl or $C_5$ to $C_{30}$ aralkyl group (with a $C_1$ to $C_8$ alkyl group);

(ii) (meth)acrylamides chosen from $CH_2$=CHCONR4R5 and $CH_2$=$C(CH_3)$CONR4R5 wherein R4 and R5, which may be identical or different, are chosen from
a) a hydrogen atom;
b) a linear or branched alkyl group comprising from 1 to 18 carbon atoms, wherein said alkyl is optionally intercalated with at least one heteroatom selected from O, N, S and P; wherein said alkyl group is optionally substituted by at least one substituent selected from
hydroxyl groups,
halogen atoms and
Si(R4R5), wherein R4 and R5, which are identical or different, are chosen from $C_1$ to $C_6$ alkyl groups and phenyl groups;
c) a C3 to C12 cycloalkyl group, or a heterocycloalkyl group, wherein the alkyl has 1 to 4 carbon atoms;
d) a C4 to C20 aryl group, and
e) a C5 to C30 aralkyl group, with a C1 to C8 alkyl group;

(iii) ethylenically unsaturated monomers comprising at least one carboxylic, phosphoric or sulphonic acid or anhydride function;

(iv) vinyl ethers chosen from R6O—CH=$CH_2$ and R6-COO—CH=$CH_2$ wherein R6 is chosen from linear or branched alkyl groups comprising from 1 to 22 carbon atom; cyclic alkyl groups comprising from 3 to 6 carbon atoms and aromatic groups;

(v) vinyl compounds chosen from $CH_2$=CH—R9, $CH_2$=CH—$CH_2$—R9 and $CH_2$=$C(CH_3)$=$CH_2$—R9 wherein R9 is chosen from hydroxyl, chlorine, fluorine, $NH_2$ groups and OR10 wherein R10 is chosen from
phenyl groups;
$C_1$ to $C_{12}$ alkyl groups wherein the monomer is a vinyl or allyl ether;
acetamide groups ($NHCOCH_3$);
OCOR11 wherein R11 is chosen from
alkyl groups comprising from 2 to 12 carbons which is linear or branched, wherein the monomer is a vinyl or allyl ester;
linear or branched alkyl groups of 1 to 18 carbon atoms, wherein said alkyl is optionally intercalated with at least one heteroatom selected from O, N, S and P, wherein said alkyl group is optionally substituted by at least one substituent selected from hydroxyl groups, halogen atoms and Si(R4R5), wherein R4 and R5, which may be identical or different, are chosen from $C_1$ to $C_6$ alkyl groups and phenyl groups;
$C_3$ to $C_{12}$ cycloalkyls;
$C_3$ to $C_{20}$ aryl groups;
$C_4$ to $C_{30}$ aralkyl groups with a $C_1$ to $C_8$ alkyl group;
4- to 12-membered aromatic or non-aromatic heterocyclic groups comprising at least one heteroatom selected from O, N and S, and
heterocycloalkyl groups with a $C_1$ to $C_4$ alkyl group;

(vi) styrene and its derivatives; and (vii) ethylenically unsaturated monomers comprising at least one silicon atoms.

18. A hyperbranched copolymer according to claim 17, wherein R is chosen from methyl, ethyl, propyl, isopropyl, n-butyl, isobutyl, tert-butyl, hexyl, ethylhexyl, octyl, lauryl, isooctyl, isodecyl, dodecyl, cyclohexyl, t-butylcyclohexyl, stearyl, 2-ethylperfluorohexyl, 2-hydroxyethyl, 2-hydroxybutyl, 2-hydroxypropyl, methoxyethyl, ethoxyethyl, methoxypropyl, isobornyl, phenyl, 2-phenylethyl, t-butylbenzyl, benzyl, furfurylmethyl or tetrahydrofurfurylmethyl groups; methoxy-polyoxyethylene (or POE-methyl) groups; POE-behenyl or trifluoroethyl groups; and a dimethylaminoethyl, diethylaminoethyl or dimethylaminopropyl groups.

19. A hyperbranched copolymer according to claim 17, wherein the alkyl of ii) b) is chosen from methyl, ethyl, propyl, isopropyl, n-butyl, isobutyl, tert-butyl, hexyl, isohexyl, cyclohexyl, ethylexyl, octyl, isooctyl, decyl, isodecyl, cyclodecyl, dodecyl, cyclododecyl, isononyl, lauryl, t-butylcyclohexyl or stearyl groups; 2-ethylperfluorohexyl groups; $C_{1-4}$ hydroxyalkyl groups; and $C_{1-4}$ alkoxy-$C_{1-4}$ alkyl groups.

20. A hyperbranched copolymer according to claim 17, wherein the ethylenically unsaturated monomers comprising at least one carboxylic, phosphoric or sulphonic acid or anhydride function are chosen from acrylic acid, methacrylic acid, crotonic acid, maleic anhydride, itaconic acid, fumaric acid, maleic acid, styrenesulphonic acid, vinylbenzoic acid, vinylphosphoric acid or acrylamidopropanesulphonic acid; and the salts thereof.

21. A hyperbranched copolymer according to claim 16, wherein the additional monomer is selected from methyl, ethyl, n-propyl, isopropyl, n-butyl, t-butyl, cyclohexyl, methoxyethyl, ethoxyethyl, trifluoroethyl, dimethylaminoethyl, diethylaminoethyl, 2-hydroxypropyl and 2-hydroxyethyl (meth)acrylates; acrylic acid, methacrylic acid, (meth)acrylamide, methacryloyloxypropyltrimethoxysilane, methacryloyloxypropyltris(trimethylsiloxy)silane; and their salts; and mixtures thereof.

22. A hyperbranched copolymer according to claim 16, wherein the additional monomer is selected from carbon or silicone macromonomers having at least one polymerizable end group.

23. A hyperbranched copolymer according to claim 16, wherein the additional monomer is selected from vinyl and (meth)acrylate groups.

24. A hyperbranched copolymer according to claim 22, wherein the macromonomer is chosen from:
(i) linear or branched $C_8$-$C_{22}$ alkyl (meth)acrylate homopolymers and copolymers having a polymerizable end group selected from vinyl and (meth)acrylate groups; poly(dodecyl acrylate) or poly(dodecyl methacrylate) macromonomers having a mono(meth)acrylate end group; and poly(stearyl acrylate) or poly(stearyl methacrylate) macromonomers having a mono(meth) acrylate end group,
(ii) polyolefins having an ethylenically unsaturated end group; and
(iii) polydimethylsiloxanes having a mono(meth)acrylate end group.

25. A hyperbranched copolymer according to claim 24, wherein the polyolefins having an ethylenically unsaturated end group are chosen from polyethylene macromonomers, polypropylene macromonomers, polyethylene/polypropylene copolymer macromonomers, polyethylene/polybutylene copolymer macromonomers, polyisobutylene macromonomers; polybutadiene macromonomers; polyisoprene macromonomers; and poly(ethylene/butylene)-polyisoprene macromonomers, wherein the macromonomer has (meth)acrylate end group.

26. A hyperbranched copolymer according to claim 24, wherein the polydimethylsiloxanes having a mono(meth)acrylate end group are chosen from compounds of formula (IIa):

$$\left| H_2C=\underset{\underset{O}{\|}}{\overset{R_8}{C}}-C-O-R_9-\underset{\underset{CH_3}{|}}{\overset{CH_3}{Si}}-O-\left[\underset{\underset{CH_3}{|}}{\overset{CH_3}{Si}}-O\right]_n\underset{\underset{CH_3}{|}}{\overset{CH_3}{Si}}-R_{10} \right| \quad (IIa)$$

wherein:
- $R_8$ is chosen from a hydrogen atom and a methyl group;
- $R_9$ is chosen from a linear or branched divalent hydrocarbon group having 1 to 10 carbon atoms and optionally comprising one or two ether bonds —O—;
- $R_{10}$ is chosen from a linear or branched alkyl group having 1 to 10 carbon atoms; and
- n is chosen from an integer ranging from 1 to 300.

27. A hyperbranched copolymer according to claim 1, comprising at least one "high Tg" branch or polymeric sequence having a Tg greater than or equal to 20° C.

28. A hyperbranched copolymer according to claim 27, wherein the at least one "high-Tg" branch is present in an amount greater than or equal to 50% by weight, relative to the total weight of the hyperbranched copolymer.

29. A hyperbranched copolymer according to claim 1, comprising at least one "low-Tg" branch or sequence having a Tg less than 20° C.

30. A hyperbranched copolymer according to claim 29, wherein the at least one "low-Tg" branch is present in an amount less than 50% by weight, relative to the total weight of the hyperbranched copolymer.

31. A hyperbranched copolymer according to claim 27, wherein the at least one "high-Tg" branch comprises "high-Tg" monomers present in a proportion of 30% to 100% by weight, relative to the total weight of said at least one "high-Tg" branch.

32. A hyperbranched copolymer according to claim 29, wherein the at least one "low-Tg" branch comprises low-Tg monomers present in a proportion of 30% to 100% by weight, relative to the total weight of said at least one "low-Tg" branch.

33. A hyperbranched copolymer according to claim 1, wherein the main branch is "high-Tg" having a Tg greater than or equal to 20° C. and at least one of the secondary branches is "low-Tg" having a Tg less than 20° C.

34. A hyperbranched copolymer according to claim 1, comprising at least one "high-Tg" monomer having a Tg greater than or equal to 20° C.

35. A hyperbranched copolymer according to claim 34, wherein the at least one "high-Tg" monomer is present in an amount ranging from 40% to 100% by weight, relative to the total weight of monomers present in the hyperbranched copolymer.

36. A hyperbranched copolymer according to claim 1, comprising at least one "low-Tg" monomer having a Tg less than 20° C.

37. A hyperbranched copolymer according to claim 36, wherein the at least one "low-Tg" monomer is present in an amount ranging from 0 to 60% by weight, relative to the total weight of monomers present in the hyperbranched copolymer.

38. A hyperbranched copolymer according to claim 1, comprising at least one lipophilic monomer, which is present in an amount ranging from 40% to 100% by weight, relative to the total weight of monomers present in the hyperbranched copolymer.

39. A hyperbranched copolymer according to claim 1, comprising at least one hydrophilic monomer, which is present in an amount ranging from 0% to 60% by weight, relative to the total weight of monomers present in the hyperbranched copolymer.

40. A hyperbranched copolymer according to claim 1, wherein the main branch is lipophilic.

41. A hyperbranched copolymer according to claim 1, wherein all the branches are lipophilic.

42. A hyperbranched copolymer according to claim 1, having a number-average molecular mass ranging from 2000 g/mol and 1500 000 g/mol.

43. A hyperbranched copolymer according to claim 1, soluble at a concentration of at least 3% by weight in isododecane at 25° C. and 1 atm.

44. A hyperbranched copolymer obtained by a process comprising:
- a first step comprising free-radical polymerization in the presence of at least one polyfunctional compound comprising at least two polymerizable functional groups, and a at least one monomer selected from isobornyl acrylate and isobornyl methacrylate; and
- a second step comprising the free-radical polymerization of at least one monomer selected from isobornyl acrylate, isobornyl methacrylate, isobutyl acrylate, isobutyl methacrylate and 2-ethylexyl acrylate, optionally in the presence of a polyfunctional compound.

45. A hyperbranched copolymer according to claim 44, wherein the polyfunctional compound corresponds to the formula (I):

$$\left| \left[H_2C=\underset{\underset{R_b}{|}}{\overset{R_a}{C}}\right]_n R_b\left[O-\underset{\underset{O}{\|}}{C}-\underset{\underset{R_c}{|}}{C}=CH_2\right]_m \right| \quad (I)$$

wherein:
- $R_a$ and $R_c$, which may be identical or different, are each chosen from hydrogen and linear or branched alkyl radicals having 1 to 22 carbon atoms;
- $R_b$ is chosen from a linear or branched divalent alkylene groups having 1 to 22 carbon atoms, divalent cycloalkylene groups having 3 to 6 carbon atoms, divalent arylene groups having 6 to 18 carbon atoms, and divalent alkarylene group having 7 to 24 carbon atoms;
- m and n, which may be identical or different, are each chosen from 1, 2, 3 or 4.

46. A hyperbranched copolymer according to claim 45, wherein the polyfunctional compound is chosen from allyl (meth)acrylates.

47. A hyperbranched copolymer according to claim 45, wherein the polyfunctional compound is used in an amount ranging from 0.05% to 15% by weight, relative to the total weight of the hyperbranched copolymer.

* * * * *

UNITED STATES PATENT AND TRADEMARK OFFICE
CERTIFICATE OF CORRECTION

PATENT NO. : 7,423,104 B2
APPLICATION NO. : 11/192062
DATED : September 9, 2008
INVENTOR(S) : Bertrand Lion It is certified that error appears in the above-identified patent and that said Letters Patent is hereby corrected as shown below:

On the title page, item (57), line 8, "chose" should read --chosen--.

In claim 10, column 21, line 55, "weight relative" should read --weight, relative--.

In claim 10, column 21, line 58, "2-ethylexyl" should read --2-ethylhexyl--.

In claim 11, column 21, lines 62-63, "2-ethylexyl" should read --2-ethylhexyl--.

In claim 12, column 21, line 67, "with" should read --which--.

In claim 12, column 22, line 2, "with" should read --which--.

In claim 13, column 22, line 9, "2-ethylexyl" should read --2-ethylhexyl--.

In claim 13, column 22, line 10, "weight relative" should read --weight, relative--.

In claim 14, column 22, line 18, "2-ethylexyl" should read --2-ethylhexyl--.

In claim 15, column 22, line 53, "2-ethylexyl" should read --2-ethylhexyl--.

In claim 17, column 23, line 41, "fromlinear" should read --from linear--.

In claim 17, column 23, line 43, "atom;" should read --atoms;--.

In claim 17, column 23, line 54, "which is" should read --which are--.

In claim 17, column 24, line 8, "atoms." should read --atom.--.

In claim 19, column 24, line 22, "ethylexyl," should read --ethylhexyl,--.

In claim 27, column 25, line 28, ""high Tg"" should read --"high-Tg"--.

In claim 44, column 26, line 31, "and a at" should read --and at--.

UNITED STATES PATENT AND TRADEMARK OFFICE
CERTIFICATE OF CORRECTION

PATENT NO. : 7,423,104 B2
APPLICATION NO. : 11/192062
DATED : September 9, 2008
INVENTOR(S) : Bertrand Lion It is certified that error appears in the above-identified patent and that said Letters Patent is hereby corrected as shown below:

In claim 44, column 26, line 36, "2-ethylexyl" should read --2-ethylhexyl--.

In claim 45, column 26, line 51, "from a linear" should read --from linear--.

In claim 45, column 26, line 55, "group" should read --groups--.

Signed and Sealed this

Sixteenth Day of December, 2008

JON W. DUDAS
*Director of the United States Patent and Trademark Office*